United States Patent
Aboussou et al.

(10) Patent No.: US 10,895,567 B2
(45) Date of Patent: Jan. 19, 2021

(54) METHOD FOR QUANTIFYING THE PYRITIC SULFUR AND THE ORGANIC SULFUR OF A ROCK SAMPLE

(71) Applicant: IFP Energies nouvelles, Rueil-Malmaison (FR)

(72) Inventors: Anabel Aboussou, Rueil Malmaison (FR); Violaine Lamoureux-Var, Chatou (FR); Daniel Pillot, St Germain en Laye (FR); Isabelle Kowalewski, Bailly (FR); Brigitte Doligez, Paris (FR); Bruno Garcia, Neuilly sur Seine (FR); Thomas Wagner, Edinburgh (GB); James Oliver Buckman, Edinburgh (GB); Christian Marz, Leeds (GB)

(73) Assignee: IFP ENERGIES NOUVELLES, Rueil-Malmaison (FR)

( * ) Notice: Subject to any disclaimer, the term of this patent is extended or adjusted under 35 U.S.C. 154(b) by 233 days.

(21) Appl. No.: 16/127,785

(22) Filed: Sep. 11, 2018

(65) Prior Publication Data
US 2019/0079065 A1 Mar. 14, 2019

(30) Foreign Application Priority Data
Sep. 12, 2017 (FR) .................... 17 58413

(51) Int. Cl.
*G01N 33/24* (2006.01)
*G01N 31/12* (2006.01)
*G01N 31/00* (2006.01)
*G01N 25/00* (2006.01)

(52) U.S. Cl.
CPC ............ *G01N 33/24* (2013.01); *G01N 25/00* (2013.01); *G01N 31/005* (2013.01); *G01N 31/12* (2013.01); *Y10T 436/186* (2015.01); *Y10T 436/188* (2015.01)

(58) Field of Classification Search
CPC ...... G01N 25/00; G01N 31/005; G01N 31/12; G01N 33/24; Y10T 436/18; Y10T 436/182; Y10T 436/186; Y10T 436/188; Y10T 436/204998; Y10T 436/205831; Y10T 436/25875

USPC ....... 436/25, 31, 32, 84, 119, 120, 122, 123, 436/133, 134, 147, 155, 157, 164, 181
See application file for complete search history.

(56) References Cited

U.S. PATENT DOCUMENTS

| | | | | |
|---|---|---|---|---|
| 4,213,763 | A * | 7/1980 | Madec | G01N 33/24 436/32 |
| 4,845,040 | A | 7/1989 | Moon et al. | |
| 6,319,717 | B1 | 11/2001 | LaCount | |
| 8,796,035 | B2 | 8/2014 | Espitalie et al. | |
| 10,302,617 | B2 * | 5/2019 | Pillot | G01N 33/241 |
| 2008/0026471 | A1 * | 1/2008 | Lorant | G01N 33/241 436/32 |
| 2020/0003750 | A1 * | 1/2020 | Aboussou | G01N 25/00 |

FOREIGN PATENT DOCUMENTS

EP 2342557 A1 7/2011

OTHER PUBLICATIONS

Baudin et al. Organic Geochemistry, vol. 86, Jun. 29, 2015, pp. 71-80.*

* cited by examiner

*Primary Examiner* — Maureen Wallenhorst
(74) *Attorney, Agent, or Firm* — Fitch, Even, Tabin & Flannery LLP (57) ABSTRACT

A method which distinctly characterizes and quantifies the pyritic sulfur and the organic sulfur of a sedimentary rock sample. A rock sample is subjected to a heating sequence in an inert atmosphere which produces effluents resulting which are continuously oxidized. $SO_2$ is continuously measured, and a pyrolysis sulfur content and a pyrolysis pyritic sulfur content are deduced therefrom. The residue from heating in an inert atmosphere is then heated in an oxidizing atmosphere. Released $SO_2$ is continuously measured and at least an oxidation sulfur content is deduced therefrom. The pyritic sulfur content is determined from pyrolysis, a weighting function, a second parameter representing the impact of the mineral matrix and a third parameter representing the impact of the organic matrix.

22 Claims, 6 Drawing Sheets

METHOD FOR QUANTIFYING THE PYRITIC SULFUR AND THE ORGANIC SULFUR OF A ROCK SAMPLE

CROSS REFERENCE TO RELATED APPLICATION

Reference is made to French Patent Application Ser. No. 17/58.413 filed Sep. 12, 2017, which is incorporated herein by reference in its entirety.

BACKGROUND OF THE INVENTION

Field of the Invention

The present invention relates to the technical field of the petroleum industry, and more particularly to the field of exploration and exploitation of a geological formation wherein hydrocarbons are trapped and more precisely, the present invention relates to characterization and quantification of the sulfur present in a sedimentary rock, such as organic matter-rich marine clay.

Description of the Prior Art

In order to meet the growing demand for energy, the petroleum industry increasingly turns to the production of unconventional crude oils, which have higher sulfur contents than conventional oils. The sulfur content of an unconventional crude oil and the type of organosulfur compounds it contains are key parameters which indicates the quality of this oil and of the refinery products obtained therefrom. Furthermore, regulations impose increasingly low sulfur contents in refinery products. It is therefore important to be able to precisely characterize and quantify the sulfur present in the rocks these sulfur crude oils originate from.

In the case of petroleum mother rocks, the two main sulfur compounds are organic sulfur and pyritic sulfur. Quantification of the organic sulfur, independently of the pyritic sulfur, is of great importance in petroleum exploration because it provides exact knowledge of the amount of sulfur associated with the organic matter of mother rocks, which is at the origin of the sulfur present in the oil generated by these mother rocks.

In particular, distinct quantification of pyritic sulfur and organic sulfur allows:

characterizing the organic matter type of the mother rock and prediction of the quality of the oil generated by the mother rock regarding the sulfur content thereof. The characterization of the organic matter type of mother rocks is conventionally done according to the elemental Carbon (C), Hydrogen (H) and Oxygen (O) content of this organic matter. This conventional characterization of the organic matter type is achieved using the conventional Van Krevelen diagram showing the Hydrogen/Carbon (H/C) atomic ratio as a function of the Oxygen/Carbon (O/C) atomic ratio. The potential of an organic matter to generate oil depending on its H, C and O composition allows distinguishing the three organic matter types according to the petroleum potential thereof. Indeed, this diagram can be correlated with the origin and the depositional environment of the organic matter. Conventionally, organic matter of lacustrine type (type I), of marine type (type II) and of terrestrial type (type III) is distinguished. Quantification of sulfur in organic matter independently of sulfur in pyrite (or pyritic sulfur) provides an additional parameter enabling finer characterization of the organic matter type, and therefore finer characterization of the depositional environment thereof and of the type of oil it can generate.

This finer characterization is performed with the three-dimensional Van Krevelen diagram: H/C as a function of O/C and $S^{org}/C$, where $S^{org}$ is the organic sulfur content. This extended diagram allows distinguishing more precisely the various organic matter types, which in particular identify organic matters of type IS and IIS which have the same origins as types I and II, but contain sulfur, and probably deposited in an anoxic or euxinic environment. This presence of sulfur also indicates that the oil obtained from cracking this organic matter will contain more sulfur. In general, data relative to the organic matter type of the mother rock provides information about the potential of the mother rock to generate oil and about the expected oil quality, notably regarding the sulfur content thereof;

to provide an additional parameter for the oil-mother rock correlation, the oil-mother rock correlation is a very important survey to be carried out by those skilled in the art to assess the petroleum system. It makes a connection between the oils contained in a reservoir and the mother rock(s) that have generated these oils. Knowing that cracking of the mother rocks containing sulfur-rich organic matter leads to the formation of equally sulfur-rich oils and gas, a method for quantifying the sulfur present in the organic matter, independently of the sulfur in the pyrite, provides a key parameter for the oil-mother rock correlation.

Patent EP-2,342,557 (U.S. Pat. No. 8,796,035) concerning a device and a method for characterizing and quantifying sulfur in a sedimentary rock or petroleum product. More precisely, the method described in this patent comprises the following steps:

heating the sample in a pyrolysis oven in a non-oxidizing atmosphere;

oxidizing part of the pyrolysis effluents and continuously measuring the amount of $SO_2$ contained in this oxidized effluent part;

transferring the pyrolysis residues to an oxidation oven and continuously measuring the amount of $SO_2$ contained in the effluents obtained after oxidizing heating of the pyrolysis residue; and deducing therefrom the sulfur content of the sample.

However, although this method allows determination of the total sulfur content of the sample being studied, it does not allow separate quantification of the pyritic sulfur and the organic sulfur. This method allows quantifying the total sulfur content of a rock sample via measurement of the sulfur effluents released by this sample during pyrolysis, then oxidation. Two profiles corresponding to sulfur are thus obtained with the first one being during the pyrolysis phase and the second being during the oxidation phase. Regarding the pyrolysis sulfur signal, it is possible to discriminate the organic sulfur from the mineral sulfur due to pyrite as they systematically form two sufficiently distinct peaks. However, in oxidation, the signals of these two sulfur compounds merge, which prevents speciation of the organic and pyritic sulfur. Furthermore, many chemical reactions occur in the rock during analysis. If some involve at least one of organic sulfur and pyritic sulfur, then they are likely to modify their signals, which adds difficulty to determine the quantification of organic sulfur and pyritic sulfur with the method as described in the aforementioned patent.

The following documents are mentioned in the remainder of the description:

Acholla, F. V., Orr, W. L., 1993. Pyrite Removal From Kerogen Without Altering Organic Matter: The Chromous Chloride Method. Energy Fuels 7, 406-410.

Bolin, T. B., 2010. Direct Determination of Pyrite Content in Argonne Premium Coals by the Use of Sulfur X-ray Near Edge Absorption Spectroscopy (S-XANES). Energy and Fuels 24, 5479-5482.

Canfield, D. E., Raiswell, R., Westrich, J. T., Reaves, C. M., Berner, R. A., 1986. The Use of Chromium Reduction in the Analysis of Reduced Inorganic Sulfur in Sediments and Shales. Chemical Geology 54, 149-155.

Orr W., 1986, "Kerogen/Asphaltene/Sulfur Relationships in Sulfur-Rich Monterey Oils", Org. Geochem. Vol. 10, pp. 499-516, 1986.

Vairavamurthy, M. A., Maletic, D., Wang, S., Manowitz, B., Eglinton, T., Lyons, T., 1997. Characterization of Sulfur-Containing Functional Groups in Sedimentary Humic Substances by X-ray Absorption Near-Edge Structure Spectroscopy. Energy and Fuels 11, 546-553.

Vandenbroucke, M., Largeau, C., 2007. Kerogen Origin, Evolution and Structure. Organic Geochemistry 38, 719-833.

There are known laboratory methods allowing distinct quantifying pyritic sulfur and organic sulfur, such as the following techniques:

Elemental analysis of kerogens, as described in the document (Vandenbroucke and Largeau, 2007). It is one of the commonest methods routinely used in the laboratory. It is carried out in 2 steps:

Kerogen isolation (or organic matter isolation) The kerogen is isolated from the raw rock through a series of chemical attacks using hydrochloric and hydrofluoric acid which destroys the mineral matrix, the carbonates and the silicates. Since pyrite ($FeS_2$), other metal sulfides and some minor oxides, including iron oxides, withstand these various chemical attacks and remain within the resultant organic residue. Thus, a kerogen which is freed from the mineral matrix is obtained but still contains pyrite;

Elemental analysis of iron (by Inductively Coupled Plasma-Atomic Emission Spectrometry ICP-AES) and sulfur (by infrared analysis) It is assumed here that the iron present in the kerogen obtained only comes in form of pyrite ($FeS_2$). Therefore, from the measurement of the iron content (ICP-AES) of the kerogen, the pyrite content can be stoichiometrically calculated, thus allowing the pyritic sulfur content to be determined. The organic sulfur content can then be deduced from the measurement of the sulfur content (IR) of the kerogen, by a difference between the total sulfur (IR measurement) and the pyritic sulfur.

This first laboratory method according to the prior art involves the following drawbacks:

duration of analysis time is about a week;

it requires preparation and chemical separation steps that are extensive and dangerous since they use strong acids;

it does not enable measurement automation;

it is based on the assumption that all of the iron contained in the organic matter is pyritic. But, if the iron contained in the organic matter also comes in other forms, such as oxides or sulfides other than $FeS_2$, the pyritic sulfur content is overestimated and the organic sulfur content is underestimated.

Pyrite extraction by chromium II chloride and by elemental analysis of the original rock, as described in documents (Canfield et al., 1986; Acholla and Orr, 1993). According to this approach, a hot hydrochloric acid (HCl) attack is first carried out in order to extract all of the volatile sulfur contained in rock samples. Once this step has been completed, the samples are heat treated with a solution of hydrochloric acid (HCl) and chromium II chloride ($CrCl_2$) allowing the pyrite ($FeS_2$) to be extracted. The sulfur effluent ($H_2S$) released by the reduction of the pyrite by this solution passes through a trap of a silver nitrate solution ($AgNO_3$), where it precipitates in a form of silver sulfide ($Ag_2S$). The $Ag_2S$ precipitate obtained is weighed, which allows stoichiometric quantification of the pyritic sulfur content, assuming that the pyrite has been entirely converted to silver sulfide. The organic sulfur content is then deduced by difference between the total sulfur content, obtained by elemental analysis of the original rock, and the pyritic sulfur content. This method is based on the assumption that all of the pyrite is reduced to $H_2S$.

This second laboratory method according to the prior art involves the following drawbacks:

it requires preparation and chemical separation steps that are extensive and dangerous since they use strong acids;

it does not enable measurement automation;

it is based on the assumption that all of the pyrite is reduced to $H_2S$. If part of the pyrite is not reduced, the pyritic sulfur content is underestimated and the organic sulfur content is overestimated. In particular, this may be the case for pyrite-rich samples.

Sulfur X-ray Absorption Near Edge Structure (S-XANES), as described in documents (Vairavumuthy et al., 1997; Bolin, 2010): according to this approach, the S-XANES technique provides information about the oxidation state of the sulfur compounds. In a typical analysis, the spectrum of a sample is deconvoluted with various linear combinations of spectra of different sulfur standards. The best adjustment is selected to indicate the real composition of the various sulfur compounds of this sample. This technique thus allows to quantitatively determine the pyritic sulfur, the organic sulfur and the sulfates. In the case of rock analysis, it is noted that very fine grinding of the sample is often necessary to better quantify the pyritic sulfur, whose peak is attenuated if the ground samples were not finely ground.

This third laboratory method according to the prior art involves the following drawbacks:

it requires very fine grinding of the samples;

it requires access to a synchrotron, which is a very heavy and expensive equipment.

SUMMARY OF THE INVENTION

The present invention addresses these drawbacks. Thus, the present invention relates to a method for characterizing the sulfur present in a rock sample, by distinctly quantifying the pyritic sulfur and the organic sulfur, in a fast, simple and precise manner.

The invention relates to a method for quantifying the pyritic sulfur in a sedimentary rock sample, wherein at least the following steps are carried out:

A. heating the sample in an inert atmosphere, between a first temperature ranging between 100° C. and 320° C. and a second temperature ranging between 600° C. and 700° C., by following a first temperature gradient ranging between 1° C./min and 30° C./min;

B. continuously oxidizing at least part of the effluents obtained from heating the sample in an inert atmosphere, continuously measuring a first amount of $SO_2$ released as a function of the time of the heating in an inert atmosphere, and determining at least a pyrolysis sulfur content $S_{Pyrol}$ and a pyrolysis pyritic sulfur content $S_{Pyrol}^{Pyrit}$ from the first amount of $SO_2$;

C. heating in an oxidizing atmosphere the residue of the sample resulting from the heating in an inert atmosphere between a third temperature ranging between 280° C. and 320° C. and a fourth temperature equal to or greater than 800° C., by following a second temperature gradient ranging between 1° C./min and 30° C./min;

D. continuously measuring a second amount of $SO_2$ released as a function of the time of the heating in an oxidizing atmosphere, determining at least an oxidation sulfur content $S_{Oxy}$ from the second amount of $SO_2$ and determining at least a total sulfur content $S_{Total}$ by the sum of the pyrolysis sulfur content $S_{Pyrol}$ and the oxidation sulfur content $S_{Oxy}$.

According to the invention, at least pyritic sulfur content $S^{Pyrit}$ of the sample is determined from a formula of the type:

$$S^{Pyrit} = p(\alpha,\beta,\gamma) \cdot S_{Pyrol}^{Pyrit},$$

where $p(\alpha, \beta, \gamma)$ is a weighting function depending on a parameter $\alpha$ representing a proportion of the pyrolysis pyritic sulfur relative to the total sulfur, a parameter $\beta$ representing an effect of the mineral matrix on said proportion, a parameter $\gamma$ representing an effect of the organic matrix on said proportion with the values of the parameters being predetermined.

According to an implementation of the invention, the weighting function $p(\alpha,\beta, \gamma)$ can be written in the form:

$$p(\alpha, \beta, \gamma) = \frac{(1+\beta+\gamma)}{\alpha}$$

According to an embodiment of the invention, the sample is a type of reservoir rock and the first temperature can range between 100° C. and 200° C.

According to another embodiment of the invention, the sample is a type of mother rock and the first temperature can range between 280° C. and 320° C.

According to an implementation of the invention, parameter $\alpha$ can range between 0.40 and 0.46, and its value preferably is 0.43.

According to a variant embodiment of the invention, the rock sample is a type of clay, and parameter $\beta$ can range between 0.04 and 0.7, and its value preferably is 0.38.

According to another variant of the invention, the rock sample is a type of marl, and parameter $\beta$ can range between 0.7 and 0.9, and its value preferably is 0.78.

According to an alternative variant of the invention, the rock sample is a type of limestone, and parameter $\beta$ can range between 0.85 and 0.97, and its value preferably is 0.9.

According to an embodiment of the invention, the rock sample contains organic matter of at least one lacustrine and marine origin, and the value of parameter $\gamma$ is 0.

According to another embodiment of the invention, the rock sample contains an organic matter of terrestrial origin, and parameter $\gamma$ can range between 0.23 and 0.29, and its value preferably is 0.26.

According to a variant embodiment of the invention, the fourth temperature ranges between 800° C. and 900° C., and an organic sulfur content $S^{Org}$ can be determined according to the formula:

$$S^{Org} = S_{Total} - S^{Pyrit}.$$

According to another variant of the invention, the fourth temperature is greater than 1150° C. and is preferably less than 1250° C., and a sulfate sulfur content $S_{Oxy}^{Sulfa}$ a can be additionally determined from said second amount of $SO_2$, and an organic sulfur content can be deduced therefrom with the formula:

$$S^{Org} = S_{Total} - S^{Pyrit} - S_{Oxy}^{Sulfa}.$$

According to an implementation of the invention, at least one of the pyrolysis sulfur content and the pyrolysis pyritic sulfur content can be determined from the first amount of $SO_2$ and from a pyrolysis sulfur calibration coefficient established on a reference sample whose sulfur content is known, with the reference sample preferably being native sulfur.

According to an implementation of the invention, the oxidation sulfur content can be determined from the second amount of $SO_2$ and from an oxidation sulfur calibration coefficient established on a reference sample whose sulfur content is known. The reference sample is preferably coal.

Advantageously, it is further possible to measure:
amounts of hydrocarbon products, of CO and $CO_2$ contained in the effluents resulting from the heating of the sample in an inert atmosphere, and
the amounts of CO and $CO_2$ contained in the effluents resulting from the heating of the effluents resulting from the heating in an oxidizing atmosphere.

BRIEF DESCRIPTION OF THE DRAWINGS

Other features and advantages of the method according to the invention will be clear from reading the description hereafter of embodiments given by way of non limitative example, with reference to the accompanying drawings wherein.

DETAILED DESCRIPTION OF THE INVENTION

In general terms, one object of the invention is a method for distinctly quantifying the pyritic sulfur and the organic sulfur present in a rock sample.

The present invention may apply to any type of sedimentary rocks such as, for example, a mother rock, a reservoir rock or an unconventional mother rock. In particular, the present invention is suited for rock samples from marine mother rocks.

In general, the rock sample may have been taken for example by coring within an underground formation of interest or it may result from drill cuttings. Advantageously, the sample as taken is prepared (by washing, screening, sorting, etc.) to remove impurities (drilling mud for example, pollutants, etc.), then it is hand ground or mechanically crushed.

The method according to the invention is based on the measurement of the sulfur dioxide ($SO_2$) released by a rock sample first subjected to pyrolysis (that is heating in an inert atmosphere), then to oxidation (that is heating in an oxidizing atmosphere).

The method according to the invention can be advantageously, but is not limited to using the ROCK-EVAL® device (IFP Energies nouvelles, France), as described in patent EP-2,342,557 (U.S. Pat. No. 8,796,035).

The method according to the invention comprises at least the following steps:
1. Heating sequence in an inert atmosphere (pyrolysis)
2. Heating sequence in an oxidizing atmosphere (oxidation)
3. Pyritic sulfur quantification.

1. Heating Sequence in an Inert Atmosphere (Pyrolysis)

In this step, the sample being considered is heated in an inert atmosphere (such as, for example, in a stream of nitrogen, helium) according to a predetermined time-varying temperature program.

According to an implementation of the invention, this step is carried out using a pyrolysis oven, the sample of interest placed in the oven being swept by a non-oxidizing gas stream.

According to the invention, the sample is heated by pyrolysis between a temperature T1 ranging between 100° C. and 320° C., and a temperature T2 ranging between 600° C. and 700° C., preferably 650° C., with the temperature rise following a temperature gradient (or heating rate) ranging between 1° C./min and 30° C./min, preferably between 20° C./min and 30° C./min, and is more preferably 25° C./min. According to an implementation of the invention where the analyzed sample is a reservoir rock, temperature T1 ranges between 100° C. and 200° C., and it is preferably 180° C. According to an implementation of the invention where the analyzed sample is a mother rock, with the temperature T1 ranging between 280° C. and 320° C., and it is preferably 300° C.

According to the invention, at least part of the pyrolysis effluents is oxidized as they are released. The sulfur gases present in the pyrolysis effluents are thus oxidized to $SO_2$.

According to an implementation of the invention, the oxidation of the pyrolysis effluents is performed using a combustion chamber, such as an oxidation oven, in the presence of an oxygen-containing gas and optionally of a catalyst.

According to the invention, the $SO_2$ that is generated is continuously measured as the pyrolysis progresses, using a $SO_2$ detector such as an ultraviolet (UV) or infrared (IR) spectrophotometer. A measurement of the $SO_2$ released during pyrolysis as a function of the pyrolysis time and/or temperature is thus obtained.

2. Heating Sequence in an Oxidizing Atmosphere (Oxidation)

In this second step, the solid sample residue obtained after the pyrolysis sequence as described in step 1 above is subjected to oxidation according to a predetermined time-varying temperature program.

According to the invention, the sample is heated in an oxidizing atmosphere between a temperature T3 ranging between 280° C. and 320° C., preferably 300° C., and a temperature T4 greater than or equal to 800° C., the temperature rise follows a temperature gradient (or heating rate) ranging between 1° C./min and 30° C./min, preferably between 20° C./min and 30° C./min, and it is most preferably 20° C./min.

According to an implementation of the invention, this step is carried out using an oxidation oven with the pyrolysis residue being swept by an air stream.

According to the invention, the $SO_2$ generated by the oxidation of the pyrolysis residue and contained in the oxidation effluents is continuously measured, that is during the heating sequence in an oxidizing atmosphere. The $SO_2$ measurement is for example performed using a UV or IR spectrophotometer. A measurement of the $SO_2$ released during oxidation, for example as a function of at least one of the oxidation time and temperature, is thus obtained.

3. Pyritic Sulfur Quantification

After carrying out the previous two steps, two curves are generated which are representative of the $SO_2$ measurements performed in steps 1 and 2 as described above.

Figure 1A:
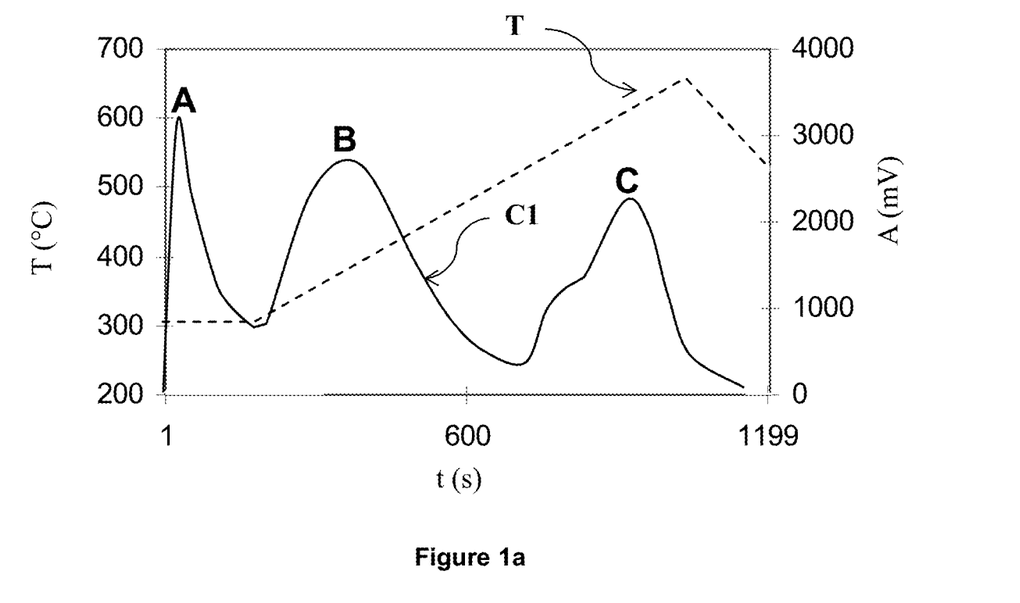
FIG. 1a shows an example of a measurement performed with a $SO_2$ detector during a heating sequence in an inert atmosphere to which a rock sample is subjected.
Figure 1B:
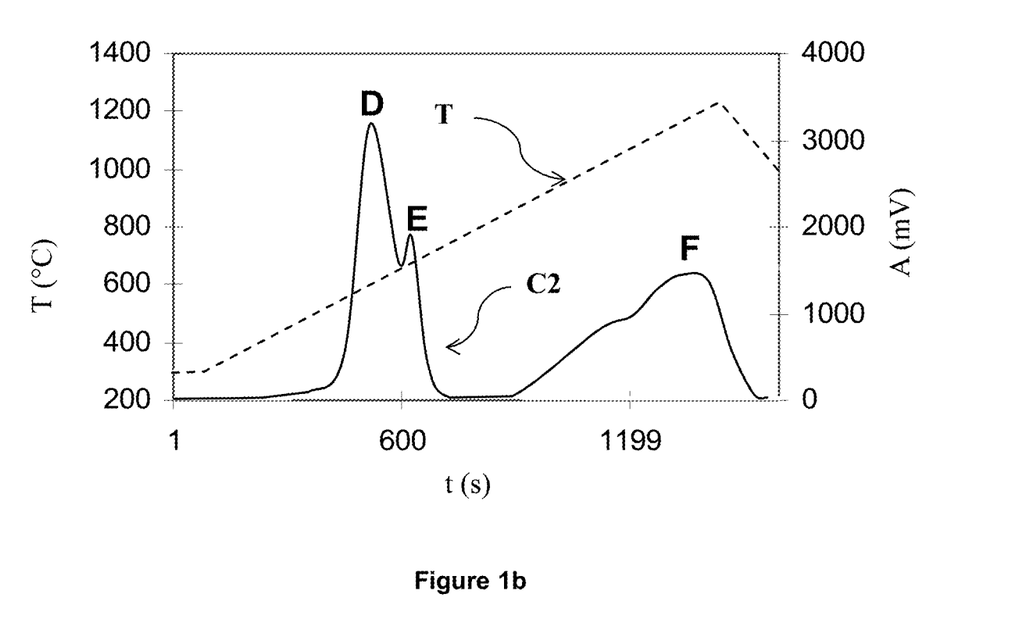
FIG. 1b shows an example of a measurement performed with a $SO_2$ detector during a heating sequence in an oxidizing atmosphere to which a rock sample is subjected.

FIG. 1a illustrates an example of a curve (C1) showing the measured amount of $SO_2$ (more precisely amplitude A measured by a $SO_2$ detector such as an ultraviolet spectrophotometer) as a function of the pyrolysis time (denoted by t), and it also shows the evolution of the pyrolysis temperature (denoted by T) as a function of the pyrolysis time. FIG. 1b illustrates an example of a curve (C2) showing the measured amount of $SO_2$ (more precisely amplitude A measured by a $SO_2$ detector such as an ultraviolet spectrophotometer) as a function of the oxidation time (denoted by t), and it also shows the evolution of the oxidation temperature (denoted by T) as a function of the oxidation time. For this example, and by way of illustration, temperature T1 was selected equal to 300° C., temperature T2 was selected equal to 650° C., temperature T3 was selected equal to 300° C. and temperature T4 was selected equal to 1200° C.

It is observed that each one of these curves comprises peaks and are identifiable by the number of these peaks, their peak apex temperature, their shape and their area. Peak C corresponding to the release, during pyrolysis, of part of the sulfur contained in the pyrite (referred to as "pyrolysis pyritic sulfur" hereafter and denoted by $S_{Pyrol}^{Pyrit}$) can notably be observed in curve C1. Peak F corresponds to the release of the sulfur contained in the sulfates (referred to as "sulfate sulfur" hereafter and denoted by $S_{Oxy}^{Sulfa}$) during oxidation can be observed in curve C2. Furthermore, the first two peaks A and B of curve C1 correspond to the sulfur contained in the thermally labile organic compounds, which are vaporizable and thermally crackable respectively. Also, it is observed that curve C2 has two nearly-merging first peaks D and E respectively corresponding to organic sulfur contained in organic compounds, which are thermally refractory or were generated during the pyrolysis phase, and to pyritic sulfur. It can thus be noted that recording the $SO_2$ released during the oxidation step does not allow distinguishing between these two peaks and therefore between the organic sulfur and the pyritic sulfur.

In this step, according to the invention, the proportion of pyrolysis sulfur $S_{Pyrol}$ released during pyrolysis, the proportion of oxidation sulfur $S_{Oxy}$ released during oxidation of the pyrolysis residue and the proportion of pyrolysis pyritic sulfur $S_{Pyrol}^{Pyrit}$ released during pyrolysis are quantified from the measurements performed during the heating sequence in an inert atmosphere and the heating sequence in an oxidizing atmosphere.

According to an implementation of the invention, the proportion of pyrolysis sulfur $S_{Pyrol}$ (respectively the proportion of oxidation sulfur $S_{Oxy}$) in the analyzed sample can be determined from the area under the measured $SO_2$ curve recorded during the pyrolysis heating sequence (respectively during the oxidizing heating sequence), divided by the mass of the analyzed sample, weighted by a pyrolysis sulfur calibration coefficient (respectively an oxidation sulfur calibration coefficient). These proportions are expressed in mass percent, that is in mass of pyrolysis sulfur (respectively of oxidation sulfur), divided by the mass of the sample and multiplied by 100.

According to an implementation of the invention, the proportion of pyrolysis pyritic sulfur $S_{Pyrol}^{Pyrit}$ can be determined from the area under the peak representative of the pyrolysis pyritic sulfur on the measured $SO_2$ curve recorded during the pyrolysis phase (see peak C in FIG. 1a), divided by the mass of the analyzed sample and weighted by a pyrolysis sulfur calibration coefficient. The proportion of pyrolysis pyritic sulfur is expressed in mass percent, that is in mass of pyrolysis pyritic sulfur, divided by the mass of the sample and multiplied by 100.

According to an implementation of the invention, a pyrolysis sulfur calibration coefficient (respectively an oxidation sulfur calibration coefficient) can be determined from at least one reference sample whose sulfur content is known, the sample being subjected to a pyrolysis heating sequence (respectively an oxidizing heating sequence). Thereafter, the pyrolysis sulfur calibration coefficient is determined from the area under the measured curve of the $SO_2$ released by this reference sample during a pyrolysis heating sequence (respectively during an oxidizing heating sequence), itself divided by the mass of the reference sample. According to an implementation of the invention, the reference sample can be native sulfur for determining the pyrolysis sulfur calibration coefficient. According to an implementation of the invention, the reference sample can be coal for determining the oxidation sulfur calibration coefficient.

According to the invention, the total sulfur content $S_{Total}$ is further determined as the sum of the two contents $S_{Pyrol}$ and $S_{Oxy}$, i.e.:

$$S_{Total} = S_{Pyrol} + S_{Oxy},$$

expressed in mass percent (wt. %), i.e. in mass of total sulfur divided by the mass of the sample and multiplied by 100.

According to the invention, the pyritic sulfur content $S^{Pyrit}$ is determined with a formula of the type:

$$S^{Pyrit} = p(\alpha,\beta,\gamma) \cdot S_{Pyrol}^{Pyrit}$$

expressed in mass percent, i.e. in mass of pyritic sulfur divided by the mass of the sample and multiplied by 100, $p(\alpha, \beta, \gamma)$ being a weighting function depending on parameters $\alpha$, $\beta$ and $\gamma$, and these parameters have been previously determined, with:

parameter $\alpha$, which represents the proportion of pyritic sulfur released during the pyrolysis phase in relation to the total sulfur thereof, and can be seen as a rate of thermal degradation of the pyrite. According to an implementation of the invention, parameter $\alpha$ ranges between 0.40 and 0.46, and its value preferably is 0.43;

parameter $\beta$, which represents the impact of the mineral matrix on the proportion of pyritic sulfur released during the pyrolysis phase. Indeed, the mineral matrix reduces the amount of sulfur of the pyrite released during the pyrolysis phase. According to an aspect of the invention, parameter $\beta$ can range between 0.04 and 0.97, depending on the type of rock the sample studied has been taken from. According to an implementation of the invention where the rock sample studied is a type of clay, parameter $\beta$ can range between 0.04 and 0.7, and its value preferably is 0.38. According to an implementation of the invention where the rock sample being studied is a type of marl, parameter $\beta$ can range between 0.7 and 0.9, and its value preferably is 0.78. According to an implementation of the invention where the rock sample studied is of limestone type, parameter $\beta$ can range between 0.85 and 0.97, and its value preferably is 0.90;

parameter $\gamma$, which represents the impact of the organic matrix on the proportion of pyritic sulfur released during the pyrolysis phase. According to an implementation of the invention, parameter $\gamma$ can range between 0 and 0.29, depending on the type of organic matter. According to an implementation of the invention where the organic matter present in the rock sample studied is a type of marine or lacustrine rock, the value of parameter $\gamma$ is 0 (no significant effect on the degradation of the pyrite during the pyrolysis phase).

According to an implementation of the invention where the organic matter present in the rock sample being studied is a type of terrestrial rock, parameter $\gamma$ can range between 0.23 and 0.29, and its value preferably is 0.26.

According to an implementation of the invention, weighting function $p(\alpha, \beta, \gamma)$ can be written in the form as follows:

$$p(\alpha, \beta, \gamma) = \frac{(1 + \beta + \gamma)}{\alpha}.$$

4. Organic Sulfur Quantification

In this step, which is optional, the proportion of organic sulfur $S^{Org}$ contained in the rock sample being considered can be determined from at least the difference between the total sulfur content $S_{Total}$ and the pyritic sulfur content $S^{Pyrit}$.

According to a first variant of the invention where the end oxidation temperature T4 ranges between 800° C. and 900° C., the proportion of organic sulfur $S^{Org}$ contained in the sample can be determined with a formula:

$$S^{Org} = S_{Total} - S^{Pyrit}$$

According to a second variant of the invention where end oxidation temperature T4 ranges between 1150° C. and 1250° C., preferably 1200° C., the proportion of organic sulfur $S^{Org}$ contained in the sample can be determined as follows:

quantifying a proportion of sulfate sulfurs $S_{Oxy}^{Sulfa}$ from the area under the peak representative of the sulfate sulfur of the measured $SO_2$ curve recorded during the oxidation step, divided by the mass of the analyzed sample and weighted by an oxidation sulfur calibration coefficient (see step 3 above for determination of this calibration coefficient);

determining the proportion of organic sulfur $S^{Org}$ with a formula of the type:

$$S^{Org} = S_{Total} - S^{Pyrit} - S_{Oxy}^{Sulfa}.$$

Indeed, for this variant embodiment, the peak $S_{Oxy}^{Sulfa}$ can be distinguished (see peak F in FIG. 1a) which corresponds to the release, during oxidation, of the sulfur contained in the sulfates, occurring at high temperatures. Determination of the organic sulfur content is more precise according to this second embodiment of the invention.

5. Calibration of Parameters α, β and γ

According to an embodiment of the invention, at least one of the parameters α, β and γ as defined above can be calibrated prior to implementing the method according to the invention, or while implementing the method according to the invention, for example prior to stage 1, stage 2 or stage 3 described above.

calibration of parameter α

According to an implementation of the invention, parameter α can be calibrated by estimating the proportion of pyritic sulfur released during the pyrolysis phase in relation to the total sulfur from at least one pure igneous pyrite sample. According to an implementation of the invention, a so-called pure pyrite can be obtained by cleaning a natural pyrite of these impurities by chemical attacks.

An example of calibration of parameter α is described hereafter. Four samples from a single pure igneous pyrite sample (respectively denoted by E1, E2, E3, E4) of different masses (respectively 2 mg, 3 mg, 4 mg and 8 mg) are each subjected to pyrolysis by the ROCK-EVAL® device (IFP Energies nouvelles, France). Notably for this example of calibration of parameter α, each sample was placed in the pyrolysis oven of the ROCK-EVAL® device and heating of the sample was carried out between 300° C. and 650° C., with a temperature ramp of 25° C./min and in a 150 ml/min nitrogen stream. Thereafter, the sulfur effluents released by each pure igneous pyrite sample being considered were carried by the nitrogen stream into the combustion chamber (oxidation oven) of the ROCK-EVAL® device, where they were converted to $SO_2$ in a continuous stream, then the $SO_2$ was carried to a $SO_2$ detector where it was continuously quantified by the $SO_2$ detector of the ROCK-EVAL® device. The solid residue of each igneous pyrite sample obtained after the pyrolysis sequence was then placed in the oxidation oven of the ROCK-EVAL® device and heating of the sample was carried out between 300° C. and 850° C., with a temperature ramp of 20° C./min and in a 100 ml/min air stream. The released $SO_2$ effluents were carried to a $SO_2$ detector where they were continuously quantified by the $SO_2$ detector of the ROCK-EVAL® device.

Figure 2:
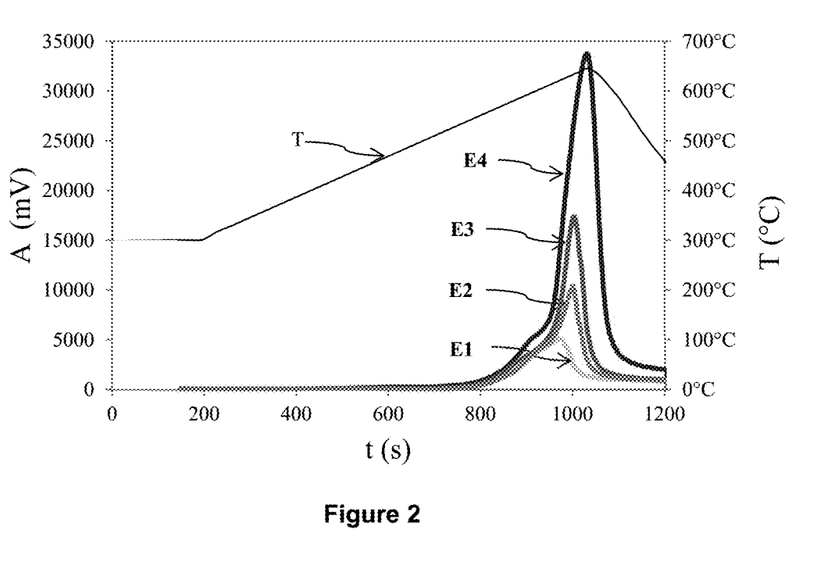
FIG. 2 shows curves representative of the amount of $SO_2$ released by four pure igneous pyrite samples of distinct masses during a heating sequence in an inert atmosphere.

FIG. 2 shows the recording over time t of the amount of $SO_2$ (more precisely the amplitude) released by samples E1, E2, E3 and E4 during the pyrolysis phase as described above. Curve T also shown in this FIG. 2 corresponds to the evolution of the temperature to which each sample considered is subjected during this pyrolysis phase. This figure notably shows the presence of peaks representative of the thermal degradation of the pyrite at the different masses analysed during the pyrolysis phase. The pyrolysis sulfur content of the igneous pyrite sample (proportion of pyrolysis pyritic sulfur) was calculated by multiplying by the sulfur content of the reference sample the area under each curve E1, E2, E3 and E4, divided by the mass of the sample, and related to the area under the measured curve of the $SO_2$ released by a reference sample (such as native sulfur) during the pyrolysis heating sequence, itself divided by the mass of the reference sample. The ratio between this pyrolysis pyritic sulfur content and the total sulfur content of the pyrite (described in step 3 above) is calculated. The results show that, whatever the mass analysed, the mass proportion of the pyritic sulfur that is released during pyrolysis is 0.43±0.03 wt %. The remaining proportion of pyritic sulfur at the end of the pyrolysis sequence (0.57±0.03 wt %) is subsequently released during the oxidation step (step 2 described above).

Thus, the calibration as described above allows a determination that parameter α ranges between 0.40 and 0.46, and its value is 0.43 on average.

calibration of parameter β

According to an implementation of the invention, the parameter β is calibrated, which represents the impact of the mineral matrix on the amount of sulfur of the pyrite released during the pyrolysis phase from at least a mixture of pyrite and of at least one mineral type. This mixture is representative of the rock sample to be studied by the method according to the invention.

An example of calibration of parameter β for various mineral types is described below. For this example of calibration of parameter β, mixtures were made from the following two major mineral groups:

clay/silicate minerals, such as:
  silica (Fontainebleau sand, France), the mixture made with silica is the reference mixture because silica is known to be non-reactive;
  kaolinite (reference: CMS Kga 1b);
  smectite (reference: Mx80);
  illite (Velay clay, France): this sample naturally containing carbonates, it was decarbonated with hydrochloric acid;
carbonate minerals, such as:
  calcite (France);
  dolomite (Euguy, Spain);
  siderite (Peru).

The following mixtures are then made:
  2 mg pyrite+98 mg of each clay/silicate mineral;
  2 mg pyrite+58 mg of each carbonate mineral;
  2 mg pyrite+98 mg clays (all the clay/silicate minerals in equal parts ¼; ¼; ¼; ¼);
  2 mg pyrite+58 mg carbonates (all the carbonate minerals in equal parts ⅓; ⅓; ⅓);
  2 mg pyrite+58 mg clays and carbonates with different proportions, i.e.:
    93% clays and 7% carbonates;
    69% clays and 31% carbonates;
    51% clays and 49% carbonates;
    26% clays and 74% carbonates.

These various samples are then subjected to steps 1 and 2 as described above using the ROCK-EVAL® device (IFP Energies nouvelles, France). More precisely, each sample is placed in the pyrolysis oven of the ROCK-EVAL® device, then heating of the sample is carried out between 300° C. and 650° C., with a temperature ramp of 25° C./min and in a 150 ml/min nitrogen stream. According to an implementation of the invention, the sulfur effluents released by each sample are carried by a nitrogen stream to the combustion chamber (oxidation oven) of the ROCK-EVAL® device, where they are converted to $SO_2$ in a continuous stream, then the $SO_2$ is carried to the $SO_2$ detector of the ROCK-EVAL® device where it is continuously quantified. The solid residue of each sample obtained after the pyrolysis sequence is then placed in the oxidation oven of the ROCK-EVAL® device and heating of the sample is carried out between 300° C. and 850° C., with a temperature ramp of 20° C./min and in a 100 ml/min air stream. The released $SO_2$ effluents are carried to a $SO_2$ detector where they are continuously quantified by the $SO_2$ detector of the ROCK-EVAL® device.

What is referred to as "mineral matrix effect" hereafter is the quantity expressed with a formula:

$$E_{Min} = \frac{S_{Pyrol}^{Pyrit,ref} - S_{Pyrol}^{Pyrit,Matrix}}{S_{Pyrol}^{Pyrit,ref}} * 100,$$

where $S_{Pyrol}^{Pyrit,ref}$ is the pyrolysis pyritic sulfur released by a reference sample (pure igneous pyrite and silica) and $S_{pyrol}^{Pyrit,Matrix}$ which is the pyrolysis pyritic sulfur released by a mixture (pure igneous pyrite plus a mineral or a mineral mixture). To evaluate this quantity, the proportion of pyrolysis pyritic sulfur is determined as described in step 3 above, for a reference sample $S_{Pyrol}^{Pyrit,ref}$ and for a considered mixture $S_{Pyrol}^{Pyrit,Matrix}$.

Figure 3A:
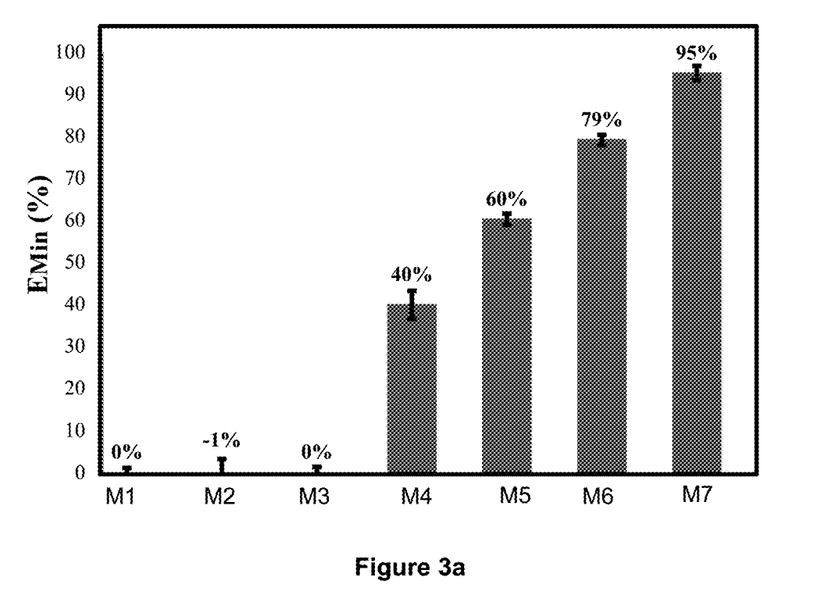
FIG. 3a shows a histogram representative of the effect of the mineral matrix as a function of the mineral mixture class being considered.

FIG. 3a shows a histogram representative of the effect $E_{Min}$ of the mineral matrix as a function of the class of mixtures considered in the case of clay/silicate and carbonate minerals, more precisely for the following mixture classes:

M1: mixtures of pyrite and quartz (reference sample);
M2: mixtures of pyrite and kaolinite;
M3: mixtures of pyrite and illite;
M4: mixtures of pyrite and smectite;
M5: mixtures of pyrite and calcite;
M6: mixtures of pyrite and dolomite;
M7: mixtures of pyrite and siderite.

Figure 3B:
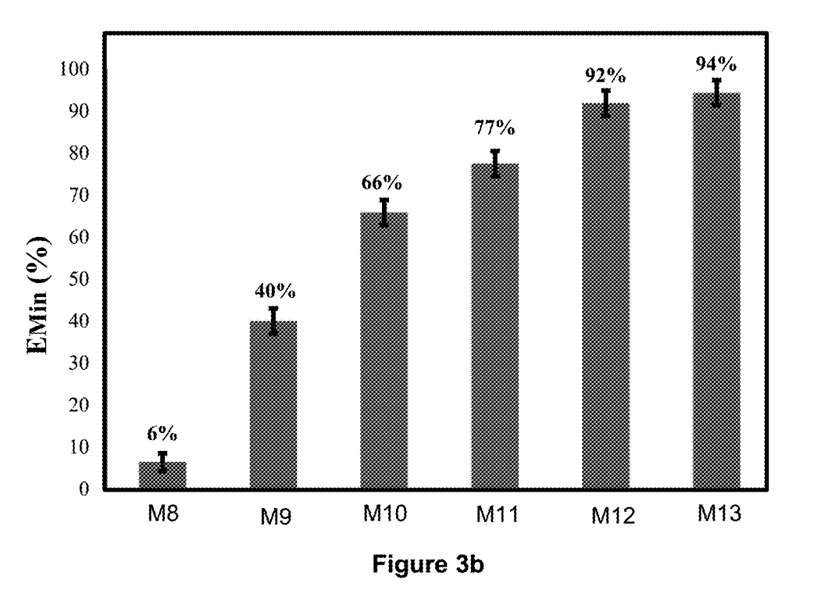
FIG. 3b shows a histogram representative of the average effect of clays, carbonates and intermediate formations on the proportion of sulfur in the pyrite released during pyrolysis as a function of the mineral mixture class being considered.

FIG. 3b shows a histogram representative of the average effect $E_{Min}$ of the clays, the carbonates and the intermediate formations on the proportion of sulfur in the pyrite released during pyrolysis for the following mixtures:

M8: mixtures of 100% clays;
M9: mixtures of 93% clays and 7% carbonates;
M10: mixtures of 69% clays and 31% carbonates;
M11: mixtures of 51% clays and 49% carbonates;
M12: mixtures of 26% clays and 74% carbonates;
M13: mixtures of 100% carbonates.

FIGS. 3a and 3b also show the error bars for each histogram bar. These error bars were obtained by estimating a standard deviation established from repeated analyses as described above.

Thus, the results obtained by implementing the method for calibrating parameter β as described above for the various mixtures described highlight that the mineral matrix can reduce the proportion of sulfur in the pyrite released during the pyrolysis phase. However, this effect is very variable depending on the type of mineral present. The relative reduction of the proportion of sulfur released by the pyrite during pyrolysis ranges between 0% and 40% in the presence of clay/silicate minerals and between 60% and 98% in the presence of carbonate minerals (see FIG. 3a). The average effect of the clays is 6%, whereas that of the carbonates reaches 93% (see FIG. 3b). An increasing evolution of the effect $E_{Min}$ of the matrix as a function of the proportion of clays and of carbonates in the mixture is observed between these two extremes (see FIG. 3b).

Figure 3C:
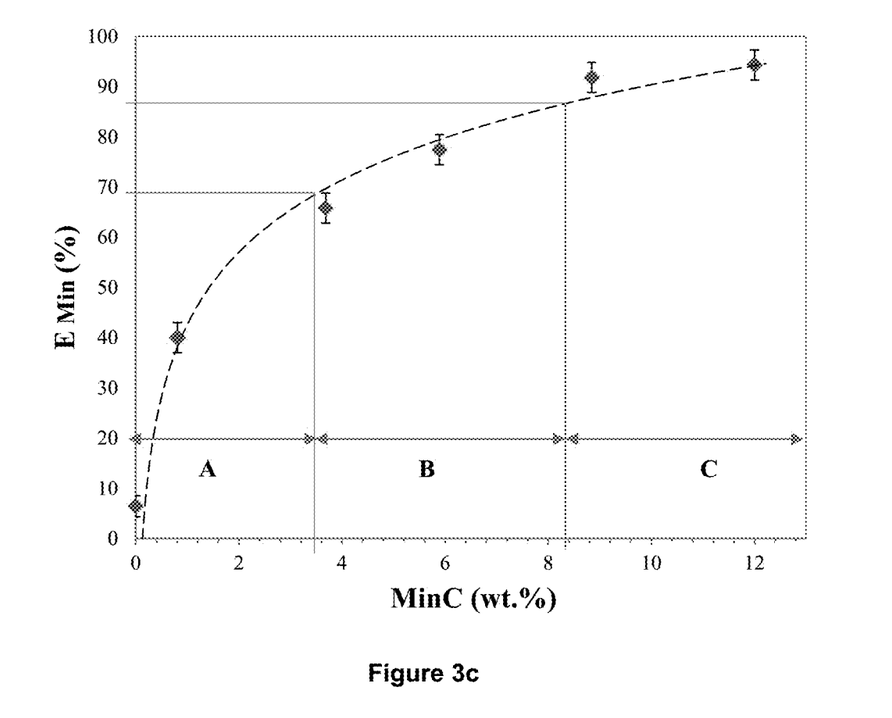
FIG. 3c shows the evolution of the effect of the mineral matrix as a function of the mineral carbon.

FIG. 3c shows the evolution of effect $E_{Min}$ of the mineral matrix as a function of the mineral carbon (denoted by MinC hereafter), a parameter that can be measured for example with the ROCK-EVAL® device (IFP Energies nouvelles, France), and which is an indicator of the carbonate content of the mixtures. It can be observed in this figure that the MinC varies in a range between 0 wt % and 12 wt %, which corresponds to a calcite equivalent between 0 wt % and 100 wt %. This parameter enables defining three types of lithology: clays, marls and limestones. Area (A) in FIG. 3c represents the area of clays with calcite equivalent carbonate contents ranging between 0 wt % and 30 wt % (0≤MinC clays<3.6 wt %). In this clay formation area, the effect of the matrix on the amount of sulfur of the pyrite released during the pyrolysis phase ranges between 6% and 70%, with an average of 38%. Area (B) in FIG. 3c represents the zone of marls, which have calcite equivalent carbonate contents ranging between 30% and 70% (3.6≤MinC marls<8.4 wt %). In this marl formation area, the average value of the matrix effect on the amount of sulfur of the pyrite released during the pyrolysis phase ranges between 70% and 87%, with an average of 78%. Area (C) in FIG. 3c represents the area of limestones with calcite equivalent carbonate contents ranging between 70 wt % and 100 wt % (8.4≤MinC limestones≤12 wt %). In this limestone formation area, the average value of the matrix effect on the amount of sulfur of the pyrite released during the pyrolysis phase ranges between 87% and 94%, with an average of 90%.

Thus, parameter β ranges between 0.06 and 0.94 depending on the type of sedimentary formation, and more precisely, in the case of:

Clays: the value of parameter β is 0.38 on average;
Marls: the value of parameter § is 0.78 on average;
Limestones: the value of parameter § is 0.90 on average.

calibration of parameter γ

According to an implementation of the invention, parameter γ is calibrated, which represents the impact of the organic matrix on the amount of sulfur released by the pyrite during the pyrolysis phase from at least a mixture of pyrite and of organic matter representative of that present in the rock sample to be studied. In natural rock samples, notably in mother rocks and in reservoir rocks in which the pyrite is found in the presence of organic matter.

An example of calibration of parameter γ is described hereafter.

According to an implementation of the invention comprising a step of calibrating parameter γ for various types of organic matter, mixtures are made of pyrite and different types of organic matter conventionally denoted by:

type I: lacustrine organic matter, such as the Green River shales (Eocene, USA);
type II: marine organic matter, such as the paper shales of the Paris Basin (Toarcian, France);
type IIS: organic sulfur-rich marine organic matter, such as the Phosphoria Formation (Permian, USA);
type III: terrestrial organic matter, such as the Calvert Bluff Formation (Paleocene, USA).

According to an implementation of the invention, mixtures such as the following can be made:

mixture of type A: 2 mg pyrite+2 mg organic matter;
mixture of type B: 2 mg pyrite+4 mg organic matter.

These mixtures are representative of a typical composition of the kerogens of sedimentary formations.

What is referred to as "organic matrix effect" hereafter is the quantity expressed with the formula as follows:

$$E_{Org} = \frac{S_{Pyrol}^{Pyrit+MO\ obtenu} - S_{Pyrol}^{Pyrit+MO\ attendu}}{S_{Pyrol}^{Pyrit+MO\ attendu}} \times 100$$

where $S_{Pyrol}^{Pyrit+MO\ obtenu}$ is the pyrolysis pyritic sulfur obtained after analysis of the mixture of pyrite and organic matter (as described in step 3) and $S_{Pyrol}^{Pyrit+MO\ attendu}$ is the expected pyrolysis pyritic sulfur value of the mixture. This theoretical reference value is calculated as follows:
- analysing each organic matter sample alone, using the ROCK-EVAL® device (IFP Energies nouvelles, France), to quantify its pyrolysis pyritic sulfur content (as described in step 3);
- analysing the pyrite alone, using the ROCK-EVAL® device (IFP Energies nouvelles, France), to quantify its pyrolysis pyritic sulfur content (as described in step 3);
- proportionally adding, as a function of the pyrite/organic matter ratio, the pyrolysis pyritic sulfur of the pyrite and the pyrolysis pyritic sulfur of the organic matter.

Figure 4A:
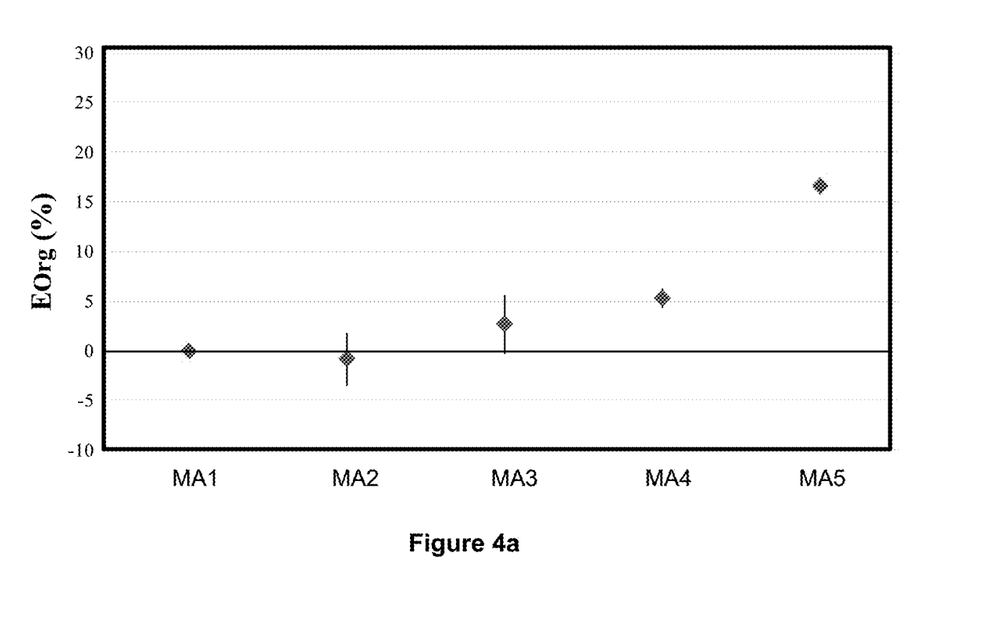
FIG. 4a shows an estimation of the effect of the organic matrix on the amount of sulfur released by the pyrite during the pyrolysis phase as a function of a first series of pyrite-organic matter mixture classes

FIG. 4a shows the effect $E_{Org}$ of the organic matrix on the amount of sulfur released by the pyrite during the pyrolysis phase for the mixtures of type A, with:
- MA1: mixture of 100% pyrite;
- MA2: mixture of 50% pyrite and 50% organic matter of type I;
- MA3: mixture of 50% pyrite and 50% organic matter of type II;
- MA4: mixture of 50% pyrite and 50% organic matter of type IIS;
- MA5: mixture of 50% pyrite and 50% organic matter of type III.

Figure 4B:
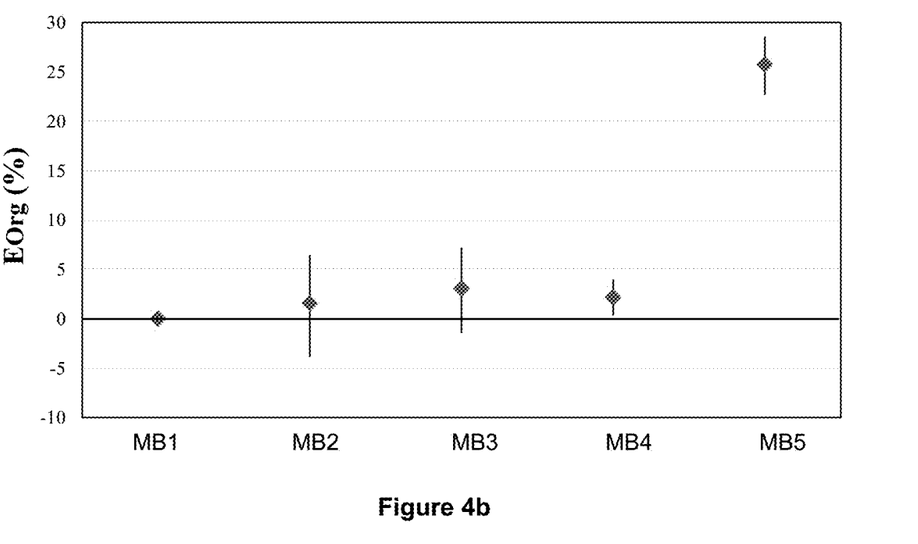
FIG. 4b shows an estimation of the effect of the organic matrix on the amount of sulfur released by the pyrite during the pyrolysis phase as a function of a second series of pyrite-organic matter mixture classes.

FIG. 4b shows the effect $E_{Org}$ of the organic matrix on the amount of sulfur released by the pyrite during the pyrolysis phase for the mixtures of type B, with:
- MB1: mixture of 100% pyrite;
- MB2: mixture of 30% pyrite and 70% organic matter of type I;
- MB3: mixture of 30% pyrite and 70% organic matter of type II;
- MB4: mixture of 30% pyrite and 70% organic matter of type IIS;
- MB5: mixture of 30% pyrite and 70% organic matter of type III.

The results obtained by implementing the method of calibrating parameter γ as described above for the various mixtures described above show that there is nearly no organic matter effect concerning types I, II and IIS. Indeed, the organic matter effect is below 6% for this mixture type (see FIGS. 4a and 4b). However, the organic matter of type III seems to have a significant effect on the amount of sulfur of the pyrite released during the pyrolysis phase (see FIGS. 4a and 4b). Indeed, the effect of the organic matter of type III is 17% on average in mixture MA5 and 26% in mixture MB5, a mixture whose proportion between pyrite and organic matter is the most representative of that of kerogens in the majority of the sedimentary formations (see FIGS. 4a and 4b).

Thus, parameter γ ranges between 0 and 0.29 depending on the type of organic matter present, and more precisely, in the case of an organic matter:
- of type I, II or IIS, the value of γ is 0 (FIGS. 4a and 4b);
- of type III, γ ranges between 0.23 and 0.29, and its value is 0.26 on average (FIG. 4b).

According to an implementation of the invention, steps 1 and 2 described above can be implemented by the ROCK-EVAL® device (IFP Energies nouvelles, France) developed by the applicant and described notably in patent EP-2,342,557 corresponding to U.S. Pat. No. 8,796,035. Indeed, the ROCK-EVAL® device comprises at least:
- a pyrolysis oven in a non-oxidizing atmosphere,
- means for oxidizing the pyrolysis sulfur effluents,
- means for continuous measurement of the amount of $SO_2$ contained in the effluents after oxidation,
- means for transferring the pyrolysis residues to an oxidation oven,
- an oxidation oven in an oxidizing atmosphere,
- means for continuous measurement of the amount of $SO_2$ contained in the part after oxidation.

Furthermore, this device can also comprise measuring the hydrocarbon compounds released during pyrolysis, as well as a detector for detecting carbon monoxide (CO) and carbon dioxide ($CO_2$).

The method can also be implemented using a single pyrolysis oven that can operate in a non-oxidizing atmosphere and in an oxidizing atmosphere, cooperating with a device for detecting and measuring the amount of sulfur dioxide ($SO_2$).

Application Examples

The method according to the invention is applied, in a first application example, to a series of thirteen samples from a rock known as Grey Shale Member, located in the Toarcian of the Whitby Mudstone Formation of the Cleveland Basin, UK. The Grey Shale Member is an interval of marine shales deposited in an oxygen-containing environment, intercalated by three sulfur-rich sedimentary layers referred to as sulfur bands. These three layers sedimented in an anoxic (oxygen-free) to euxinic (deeper, oxygen-free and beneath a sulfide-rich water layer) environment.

The method according to the invention is also applied, in a second application example, to a sample from a rock known as Black Band, which is also a shale interval of the Toarcian of the Whitby Mudstone Formation.

The method according to the invention is applied, in a third application example, to a series of eight samples from a rock known as Kimmeridge Clay Formation of the Wessex-Channel Basin in Dorset, UK. The interval studied, of the Kimmeridgian-Tithonian age, is an alternation of clays, marls and limestones.

The pyritic sulfur and the organic sulfur present in these samples are determined according to the method described above, by use of the ROCK-EVAL® device (IFP Energies nouvelles, France). More precisely, each sample is placed in the pyrolysis oven of the ROCK-EVAL® device, then heating of the sample is performed between 300° C. and 650° C., with a temperature ramp of 25° C./min and in a 150 ml/min nitrogen stream. According to an implementation of the invention, the sulfur effluents released by each sample are carried by a nitrogen stream into a combustion chamber (also referred to as oxidation oven) of the ROCK-EVAL® device, where they are converted to $SO_2$ in a continuous stream, then the $SO_2$ is carried to the $SO_2$ detector of the ROCK-EVAL® device where it is continuously quantified. After pyrolysis, each sample residue is transferred from the pyrolysis oven to the oxidation oven of the ROCK-EVAL® device and heating of the sample is carried out between 300° C. and 850° C. or 1200° C. depending on the implementation, with a temperature ramp of 20° C./min and in a 100 ml/min air stream. The $SO_2$ effluents released by this oxidation are carried to the $SO_2$ detector of the ROCK-EVAL® device where they are continuously quantified. The pyritic sulfur content and the organic sulfur content of each rock sample being analyzed are deduced by implementing the method according to the invention. Thereafter, they are compared with those obtained with the kerogen elemental analysis method described above (by ICP-AES for iron and by infrared for sulfur), referred to as method according to the prior art hereafter.

Figure 5A:
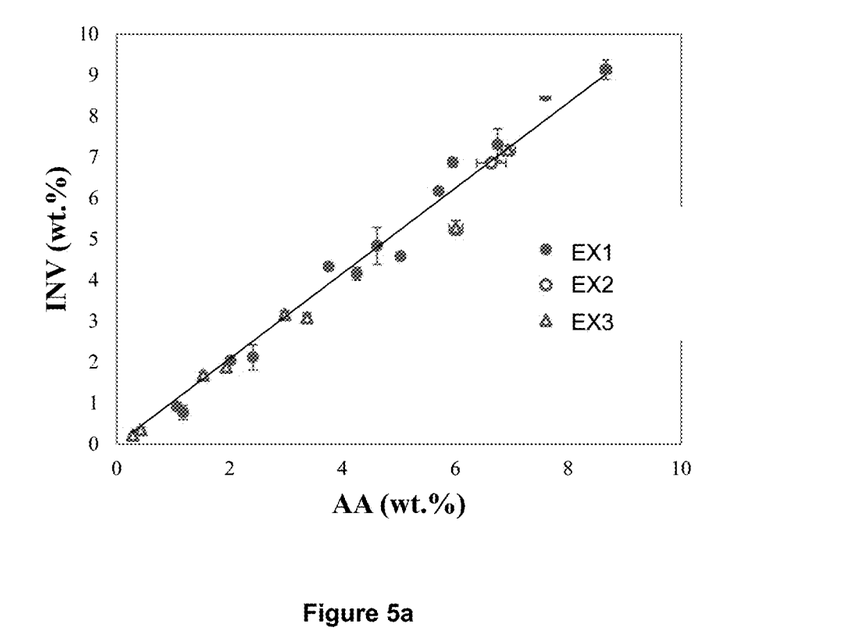
FIGS. 5a, 5b and 5c respectively show the evolution of the total sulfur, pyritic sulfur and organic sulfur content for various rock samples obtained with the method according to the invention as a function of the total sulfur content obtained for these samples with a method according to the prior art.
Figure 5B:
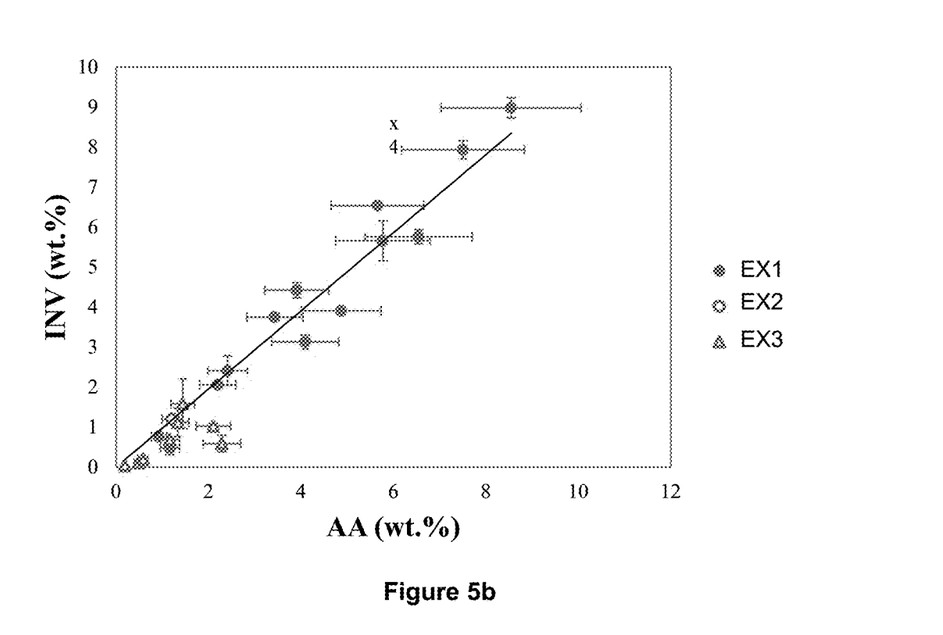
Figure 5C:
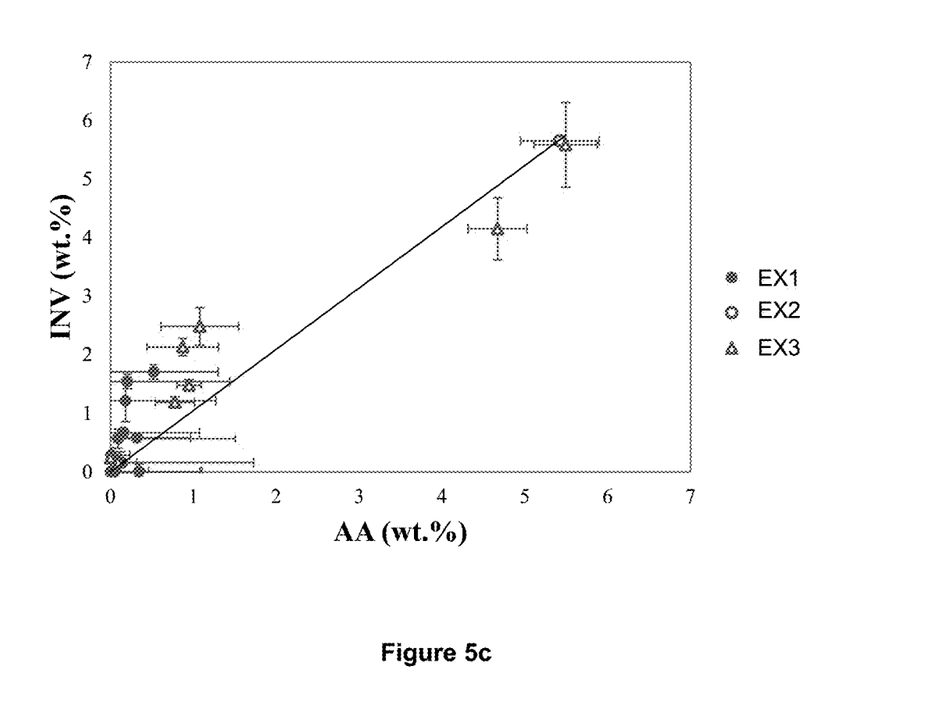

FIGS. 5a, 5b and 5c respectively show the evolution of the proportion of total sulfur, pyritic sulfur and organic sulfur in each sample of the first application example EX1 (i.e. the 13 Grey Shale Member samples), for the sample of the second application example EX2 (i.e. the Black Band sample) and for each sample of the third application sample EX3 (i.e. the 8 Kimmeridge Clay Formation samples) obtained with the method according to the invention INV, as a function of the total sulfur content obtained for the same samples with the method according to the prior art AA.

FIG. 5a shows a very strong correlation between the total sulfur contents determined with the method according to the invention and with the method according to the prior art (correlation with a slope close to 1), confirming the validity of the total sulfur content determination for a sample with the method according to the invention.

Similarly, FIG. 5b shows a very strong correlation between the pyritic sulfur contents determined with the method according to the invention and with the method according to the prior art (correlation with a slope close to 1), confirming the validity of the pyritic sulfur content determination with the method according to the invention.

FIG. 5c shows a poor correlation line concerning the organic sulfur content determined with the method according to the invention and with the method according to the prior art. In the method according to the invention, the organic sulfur content is entirely deduced from the total and pyritic sulfur contents determined with the method of the invention (see step 3 above), whose values are valid (see the discussion relative to FIGS. 5a and 5b above). This lack of correlation can be due to the fact that the majority of the samples selected have a low organic sulfur content. Indeed, the organic sulfur content of the samples selected predominantly ranges between 0 wt % and 1 wt % (prior art values) or between 0 wt % and 3 wt % (values obtained with the method according to the invention) (FIG. 5c). Thus, it is possible that the organic sulfur contents obtained here are of the order of magnitude of the measurement error of each method. Indeed, repetition of the analyses performed using the method according to the invention for various samples shows that the standard deviation on the measurement is on average 0.1 wt % for the total sulfur and 0.2 wt % for the pyritic and organic sulfur. Besides, repetition of the analyses performed using the method according to the prior art shows that the standard deviation on the measurement is on average 0.1 wt % for the total sulfur, 0.5 wt % for the pyritic sulfur and 0.6 wt % for the organic sulfur. It is therefore noted that the method according to the prior art seems to be less precise than the method according to the invention. This may be explained by the fact that the prior art combines two different techniques (ICP-AES and infrared) and therefore two possible error sources, and by the fact that this prior art is based on the assumption that all of the iron contained in the organic matter is pyritic. If the iron contained in the organic matter also comes in other forms, such as oxides or other sulfides than pyrite, the pyritic sulfur content is overestimated and the organic sulfur content is underestimated. On the other hand, the method according to the invention uses only one type of measurement (measurement of the $SO_2$ released by a sample) and it is based on a perfect distinction between the pyritic sulfur and the organic sulfur during the pyrolysis phase. Thus, the method according to the invention is less uncertain than the prior art.

Furthermore, the method of the invention is faster since the method according to the invention for the 13 Grey Shale Member samples, which as an application example described above, was conducted in about 15 hours for the 13 samples, whereas the implementation of the method according to the prior art with the same application example was conducted in about 7 days.

The invention claimed is:

1. A method for quantifying pyritic sulfur in a sedimentary rock sample, comprising:
  A. heating the sample in an inert atmosphere, between a first temperature ranging between 100° C. and 320° C. and a second temperature ranging between 600° C. and 700° C., to produce effluents by following a first temperature gradient ranging between 1° C./min and 30° C./min;
  B. continuously oxidizing at least part of the effluents obtained from heating the sample in an inert atmosphere and continuously measuring a first amount of $SO_2$ released as a function of time of the heating in an inert atmosphere, and determining at least a pyrolysis sulfur content from a area under a curve of the measured first amount of $SO_2$ released as a function of time and a pyrolysis pyritic sulfur content $S_{Pyrol}^{Pyrit}$ from a area under a last peak of the curve of the measured first amount of $SO_2$ released as a function of time;
  C. heating in an oxidizing atmosphere a residue of the sample resulting from the heating in the inert atmosphere between a third temperature ranging between 280° C. and 320° C. and a fourth temperature at least equal to 800° C., by following a second temperature gradient ranging between 1° C./min and 30° C./min;
  D. continuously measuring a second amount of $SO_2$ released as a function of time of the heating in the oxidizing atmosphere and determining at least an oxidation sulfur content from a area under a curve of the measured second amount of $SO_2$ released as a function of time and determining at least a total sulfur content $S_{Total}$ by a sum of the pyrolysis sulfur content and the oxidation sulfur content; and
wherein at least a pyritic sulfur content $S^{Pyrit}$ of the sample is determined from a formula:

$$S^{Pyrit} = p(\alpha, \alpha, \gamma) \cdot S_{Pyrol}^{Pyrit}, \text{ wherein}$$

$p(\alpha, \beta, \gamma)$ is a weighting function depending on a parameter $\alpha$ which represents a proportion of the pyrolysis pyritic sulfur relative to the total sulfur, parameter $\beta$ which represents an effect of a mineral matrix of the sedimentary rock sample on the proportion, parameter $\gamma$ which represents an effect of organic matrix of the sedimentary rock sample on the proportion with values of the parameters being predetermined.

2. A method as claimed in claim 1, wherein the weighting function $p(\alpha, \beta, \gamma)$ is written as:

$$p(\alpha, \beta, \gamma) = \frac{(1 + \beta + \gamma)}{\alpha}$$

3. A method as claimed in claim 1, wherein the sample is reservoir rock and the first temperature ranges between 100° C. and 200° C.

4. A method as claimed in claim 1, wherein the sample is mother rock and the first temperature ranges between 280° C. and 320° C.

5. A method as claimed in claim 1, wherein parameter α ranges between 0.40 and 0.46.

6. A method as claimed in claim 5, wherein α is 0.43.

7. A method as claimed in claim 1, wherein the rock sample is clay and parameter β ranges between 0.04 and 0.7.

8. A method as claimed in claim 7, wherein β is 0.38.

9. A method as claimed in claim 1, wherein the rock sample is marl and parameter β ranges between 0.7 and 0.9.

10. A method as claimed in claim 9, wherein β is 0.78.

11. A method as claimed in claim 1, wherein the rock sample is limestone and parameter β ranges between 0.85 and 0.97.

12. A method as claimed in claim 11, wherein β is 0.9.

13. A method as claimed in claim 1, wherein the rock sample contains organic matter of at least one of lacustrine and marine origin, and a value of parameter γ is 0.

14. A method as claimed in claim 1, wherein the rock sample contains an organic matter of terrestrial origin and parameter γ ranges between 0.23 and 0.29.

15. A method as claimed in claim 14, wherein γ is 0.26.

16. A method as claimed in claim 1, wherein the fourth temperature ranges between 800° C. and 900° C., and an organic sulfur content $S^{Org}$ is determined according to a formula as follows:

$$S^{Org}=S_{Total}-S^{Pyrit}.$$

17. A method as claimed in claim 1, wherein the fourth temperature is greater than 1150° C. and less than 1250° C. in step C, and a sulfate sulfur content $S_{Oxy}^{Sulfa}$ is additionally determined from a area under a last peak of the curve of the measured second amount of $SO_2$ released as a function of time in step D, and organic sulfur content is determined with a formula:

$S^{Org}=S_{Total}-S^{Pyrit}-S_{Oxy}^{Sulfa}$, wherein, $S^{Pyrit}$ is pyritic sulfur content and $S_{Total}$ is a total amount of sulfur that is present.

18. A method as claimed in claim 1, wherein at least one of the pyrolysis sulfur content and the pyrolysis pyritic sulfur content is determined from the first amount of $SO_2$ and from a pyrolysis sulfur calibration coefficient established on a reference sample whose sulfur content is known, wherein the reference sample is subjected at least to step A) and B) and the pyrolysis sulfur calibration coefficient is determined from an area under a curve of a measured amount of $SO_2$ released by the reference sample as a function of time during step A) and B).

19. A method as claimed in claim 18, wherein the reference sample is native sulfur.

20. A method as claimed in claim 1, wherein the oxidation sulfur content is determined from the second amount of $SO_2$ and from an oxidation sulfur calibration coefficient established from a reference sample whose sulfur content is known, wherein the reference sample is subjected at least to step C) and D) and the oxidation sulfur calibration coefficient is determined from an area under a curve of a measured amount of $SO_2$ released by the reference sample as a function of time during steps C) and D).

21. A method as claimed in claim 20, wherein the reference sample is coal.

22. A method as claimed in claim 1, further comprising:
measuring amounts of hydrocarbon products of CO and $CO_2$ contained in effluents that result from the heating of the sample in an inert atmosphere; and
measuring amounts of CO and $CO_2$ contained in effluents resulting from the heating in an oxidizing atmosphere.

* * * * *